United States Patent [19]
Li et al.

[11] Patent Number: 5,226,020
[45] Date of Patent: Jul. 6, 1993

[54] WRIST WATCH HAVING THE FUNCTION OF MAGNETIC HEALTH CARE

[75] Inventors: Zhi L. Li; Wen Q. Xu; Zi Q. Yu, all of Shanghai, China

[73] Assignee: Shanghai Chunlei Watch Company, Shanghai, China

[21] Appl. No.: 929,762

[22] Filed: Aug. 12, 1992

[30] Foreign Application Priority Data

Aug. 17, 1991 [CN] China .................. 91215804.2
Oct. 29, 1991 [CN] China .................. 91230852.4

[51] Int. Cl.⁵ .................. G04B 47/00; A61N 1/42
[52] U.S. Cl. .................. 368/10; 368/293; 600/9; 600/15
[58] Field of Search .................. 368/10, 276, 293, 327; 600/9, 15

[56] References Cited

U.S. PATENT DOCUMENTS

| | | | |
|---|---|---|---|
| 3,906,713 | 9/1975 | Suda et al. | 368/250 |
| 3,921,620 | 11/1975 | Nakayama | 128/1.3 |
| 4,033,111 | 7/1977 | Matsuura | 368/293 |
| 5,002,068 | 3/1991 | Provell | 128/846 |

*Primary Examiner*—Vit W. Miska
*Attorney, Agent, or Firm*—Morgan & Finnegan

[57] ABSTRACT

A wrist watch with health care function consists of a mechanism (core), a case and a back cover of a wrist watch having timekeeping function. A magnetic body is placed in the back cover of the wrist watch. Between the magnetic body and the mechanism (core) of the wrist watch is a magnetic isolating body which is formed by the back cover itself or which is a ⊔-shaped magnetic isolating shield or a magnetic isolating piece covered on the magnetic body in the back cover so that the wrist watch can both tell time (maintaining the accuracy of timekeeping) and provided the function of health care for treating or preventing from human diseases through the action of the magnetic source.

12 Claims, 2 Drawing Sheets

WRIST WATCH HAVING THE FUNCTION OF MAGNETIC HEALTH CARE

BACKGROUND OF THE INVENTION

1. Field of the Invention

The present invention relates to a timekeeping device, and particularly relates to a wrist watch having the function of magnetic health care.

2. Description of the Prior Art

At present various health care devices for treating some human body diseases using magnetic performance such as magnetic bracelet or wearable magnetic health care devices imitating the shape or appearance of a wrist watch are known or commercially available. Although such devices have the function of magnetic treatment, themselves, have no timekeeping function, i.e. they can not tell time nor show date etc.. On the contrary, the existing wrist watches known to have the timekeeping function have no function of disease treatment using magnetic performance, this is because a wrist watch must be kept away from magnetic substances. Once the mechanism of a wrist watch, including the mechanism of electronic wrist watch, has been subjected to the interference from external strong magnetic field, the performance of the elements and components thereof will be affected or degraded, resulting in error or failure in timekeeping. Therefore it is desirable that there is a kind of wrist watch which can tell time as well as offer the function of health care using magnetic performance.

The object of the present invention is to overcome the deficiency of the above-mentioned magnetic bracelet and the timekeeping wrist watch with a view to meeting the above-mentioned requirements.

SUMMARY OF THE INVENTION

In order to realize the above-mentioned object, a piece of magnetic body or magnet is added in the back cover of a timekeeping, wrist watch and at the same time a magnetic isolation body is placed between the mechanism of the wrist watch and the magnetic body. Through the action of the magnetic isolating body, the sphere of distribution of the normal magnetic force is changed and a new distribution sphere of the magnetic force is formed so that the mechanism of the wrist watch is not subjected to the interference from the added-in magnetic body and the newly defined sphere of the magnetic force is just distributed outside of the back cover of the wrist watch and can act on Jing Luo (main and collateral channels through which vital energy circulates and along which the acupuncture points are distributed according to traditional Chinese medical science) acupuncture points near the wrist of a human body, thereby realizing the dual purpose of timekeeping and magnetic health care.

According to the present invention, a wrist watch with health care function consists of a mechanism (core), a case and a back cover of a timekeeping wrist watch, a magnetic body or magnet is placed on the back cover and a magnetic isolating body is disposed between said magnetic body and the mechanism.

According to the present invention said magnetic body is disposed on the inner side of the back cover opposite to the mechanism of the wrist watch or in the back cover. Said magnetic body may consist of a single or several pieces of magnetic bodies, and the corresponding magnetic isolating body may consist of a single or several pieces of magnetic isolating bodies, and both the magnetic body and the magnetic isolating body are disposed in the respective cavities in the back cover of the wrist watch.

According to the present invention, said magnetic isolating body is a magnetic isolating piece which is covered on the magnetic body and attached on the inner side or fitted within the back cover, to form a magnetic barrier or shield. Furthermore, said magnetic isolating body may be the back cover itself, in this case, the magnetic body and the corresponding cavity receiving the magnetic body is disposed on the outer side of the back cover close to the wrist; alternatively, the magnetic isolating body may be a -shaped magnetic isolating shield covering the magnetic body in the back cover. In this case, the magnetic body, the -shaped magnetic isolating shield and the cavity receiving the magnetic body and the magnetic isolating shield are disposed on the outer side or on the inner side of the back cover.

The structure features and advantages of the present invention will be more apparent through the following detailed description of the embodiments in conjunction with the accompanying drawings.

DESCRIPTION OF THE INVENTION

Figure 1:
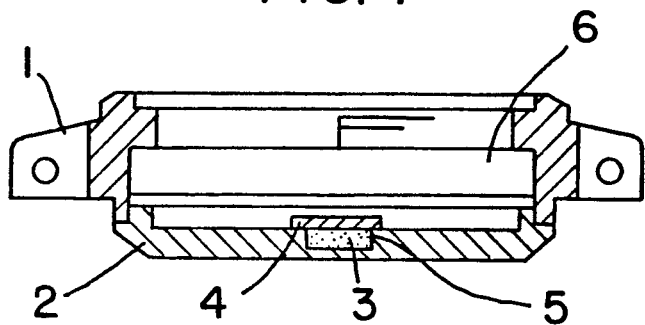
FIG. 1 is a structural schematic view of one embodiment according to the present invention wherein the magnetic isolating body is a circular magnetic isolating piece.
Figure 2:
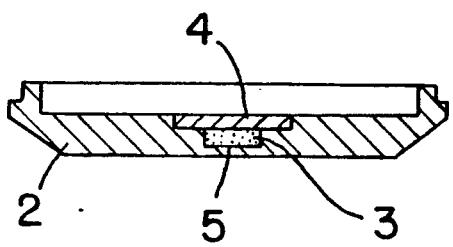
FIG. 2 and FIG. 3 show schematically the circular magnetic isolating piece, magnetic body and their corresponding cavities disposed at respective positions of the above-mentioned embodiment.
Figure 3:
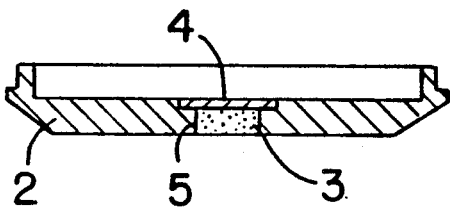

In FIGS. 1 to 3, the reference number 1 denotes the case of a wrist watch, 2, the back cover, 3, the magnetic body, 4, the magnetic isolating body, 5, the cavity for receiving the magnetic body, 6, the mechanism (core) of the wrist watch. As shown in these figures, a cavity 5 receiving the magnetic body 3 is defined on the conventional back cover 2 of a wrist watch, a piece of permanent magnetic body 3 made of rare earth magnet with the shape and size being matched with the cavity 5 is tightly fitted into the cavity 5, the magnetic induction or magnetic flux density of the magnetic body 3 is of 100-400 mili-Tesla. Then a magnetic isolating body made of pure iron or alloy, i.e. the magnetic isolating piece 4, is covered on the magnetic body 3 and is attached to the inner side of the back cover 2 (the side opposite to the mechanism (core) of the wrist watch). Finally the back cover 2 is mounted on the case 1 of the wrist watch. The magnetic isolating piece 4 and the magnetic body 3 mentioned here may be of different shapes such as circular, square or elliptic with a thickness not less than 0.20 mm, the ratio of the thickness and minimum periphery of the isolating piece to those of the magnetic body is ranging from 1:(1-4) and (1-4):1 respectively. In this embodiment, a circular magnetic isolating piece and a circular magnetic body are used. The thickness ratio between the circular magnetic isolating piece 4 and the magnetic body 3 is 1:(1-4), the ratio of their diameters is (1-4):1. The dimensions of the circular magnetic isolating piece is φ 10 mm × H0.5 mm. Thus, the circular magnetic isolating piece 4 is sandwiched between the mechanism (core) 6 and the inner side of the back cover 2 containing the magnetic body 3, forming a magnetic barrier for the mechanism of the wrist watch and at the same time, changing the distribution sphere of magnetic force of the magnetic body 3, i.e. defining a new sphere of magnetic force, which results in a magnetic source which has the function of magnetic therapy while the function of timekeeping of the wrist watch is not affected.

As shown in FIGS. 2 to 3, the magnetic body 3 and the magnetic isolating body 4 may be either disposed on the inner side of the back cover 2 or in the back cover; the magnetic body 3 may consist of a single or several bodies. Correspondingly, the cavity 5 defined on the back cover for receiving the magnetic body 3 may be either a single cavity or may consist of several cavities.

Figure 4:
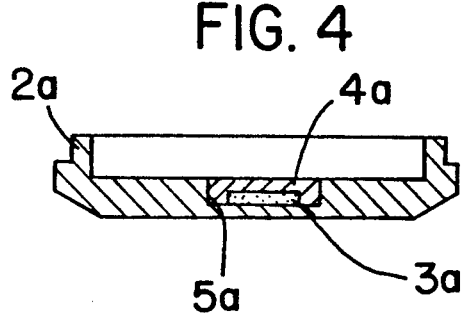
FIG. 4 and FIG. 5 show schematically the -shaped magnetic isolating shield of the other two embodiments as well as the different arrangement positions of the isolating shield, the magnetic body and their corresponding cavities.
Figure 5:
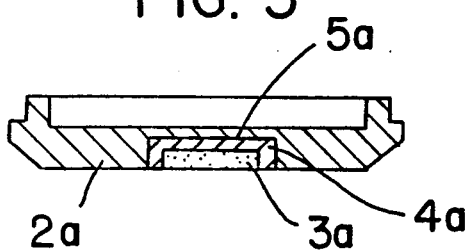
Figure 6:
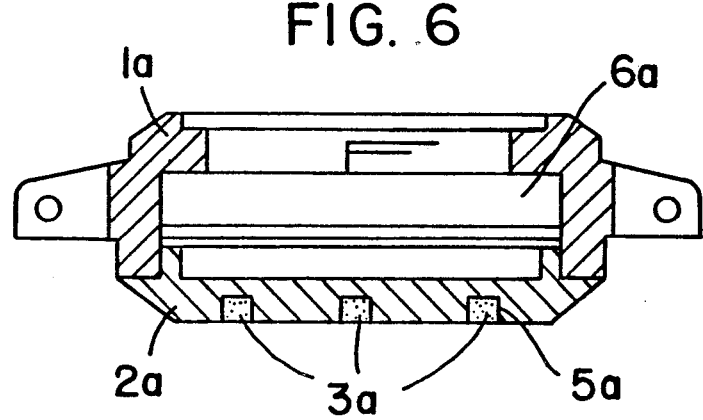
FIG. 6 shows schematically an embodiment wherein the magnetic isolating body is the back cover itself of wrist watch.

FIGS. 4 to 6 show two improvements made on the basis of the wrist watch with the function of health care shown in FIGS. 1 to 3. In these figures, 1a denotes the case of a wrist watch, 2a, a back cover, 3a, a magnetic body, 4a, a ⌊⌋-shaped magnetic isolating shield, 5a, a cavity receiving the magnetic body and magnetic isolating shield, 6a, a mechanism (core) of a wrist watch.

The embodiments shown in FIG. 4 and FIG. 5 are directed against the problem arising from the fact that a small amount of magnetic leakage may occur with the circular or otherwise shaped thin magnetic pieces. As shown in the figures, on the outer side of the back cover 2a of the wrist watch (the surface of the back cover close to the wrist) or on the inner side, a cavity 5a is defined for receiving the magnetic body 3a and the ⌊⌋-shaped magnetic isolating shield 4a with the dimensions φ 6 mm × H0.5 mm. A permanent magnetic body 3a made of Nd-Fe-B alloy with magnetic induction 100-400 mili-Tesla is disposed in the cavity 5a (the size of the permanent magnetic body 3a is slightly smaller than that of the cavity 5a and the shape of 3a is similar to that of 5a), then a material of high magnetic permeability such as pure iron sheet or plate is pressed into a ⌊⌋-shaped magnetic isolating shield 4a the dimension of which is identical with that of the cavity 5a. The internal cavity of the magnetic isolating shield 4a can accommodate the magnetic body 3a which is covered with the isolating shield 4a and this magnetic isolating shield 4a is sandwiched between the inner wall of the cavity 5a and the outer wall of the magnetic body 3a. Of course, the prefabricated magnetic body 3a may be first fitted into the magnetic isolating cover 4a to form an integral whole, and then the assembly is tightly fitted into the cavity 5a. Finally this back cover 2a is mounted on the case 1 of the wrist watch. The magnetic isolating shield 4a, due to the fact that its open end is facing toward the back cover 2a while it is fitted into the case 1, the performance of the two magnetic poles at the open end is better than that of the poles of the original circular thin magnetic isolating piece 4, together with the high magnetic permeability of the material, a ⌊⌋-shaped magnetic barrier is formed between the mechanism (core) 6 and the back cover containing the magnetic body 3, making the magnetic force (the magnetic lines of force) of the magnetic body 3 shift to outside of the back cover 2, i.e. resulting in a new sphere of distribution of the magnetic force (magnetic lines of force). Apparently the structure of ⌊⌋-shaped magnetic isolating shield has its advantage in preventing the magnetic lines of force from leaking out.

As shown in FIG. 6, according to the present invention, the ⌊⌋-shaped magnetic isolating shield 4a shown in FIG. 4 and FIG. 5 may be replaced by the back cover 2a which is simultaneously used as the magnetic isolating body 4a, i.e. the back cover is now not made of stainless steel, instead, it is directly made of materials of high magnetic permeability. On the outer side of the back cover 2a, now made of the new material, is defined a single or several cavities 5a for receiving the magnetic body 3a and the prefabricated magnetic body 3a with the corresponding shape is tightly fitted into the cavity 5a, then the portion of the opening of the cavity 5a exposed on the outer side of the back cover 2a is sealed flush with known materials and methods. Finally the back cover is mounted on the case of the wrist watch. It is obvious that, when the back cover itself of the wrist watch is used as the magnetic isolating body, due to the fact that the volume of the back cover of the wrist watch is several times larger than that of the magnetic body, and the volume of the magnetic body may be several times larger than the original one, thus the resultant magnetic force is much stronger. When one or more magnetic bodies is (are) covered with such a back cover, the magnetic isolating effect is much greater than the above-mentioned circular magnetic isolating piece or ⌊⌋-shaped magnetic isolating shield. Therefore, in this case the magnetic body with the optimum magnetic force may be used in the back cover, thereby providing a health care wrist watch with its back cover used advantageously as the magnetic isolating body.

When the wrist watch having the health care function according to the present invention is fitted with the magnetic body for treating some diseases, due to the presence of the magnetic isolating body, the inherent accuracy of timekeeping of the wrist watch is not affected and the wrist watch may be conveniently worn on the wrist. Through the action of the magnetic body on the Jing Luo (channels and collaterals) of the human body, it offers good health care effect for some of the chronic diseases such as hypertension, neurasthenia, cardiovascular disease etc..

We claim:

1. A wrist watch with health care function, comprising a mechanism (core), a case and a back cover of a wrist watch having a timekeeping function, a magnetic body installed in the back cover and a magnetic isolating body sandwiched between the magnetic body and the mechanism (core) of the wrist watch.

2. The wrist watch with health care function according to claim 1 wherein said magnetic body is placed on the inner side of the back cover opposite to the mechanism (core) of the wrist watch, and said magnetic body may consist of a single or several magnetic bodies which is (are) contained in a corresponding cavity (cavities) in the back cover.

3. The wrist watch with health care function according to claim 1 wherein said magnetic body is placed in the back cover, and said magnetic body may consist of a single or several magnetic bodies which is (are) contained in a corresponding cavity (cavities) in the back cover.

4. The wrist watch with health care according to claim 2 wherein said isolating body is a magnetic isolating piece covered on the magnetic body and attached to the inner side of the back cover to form a magnetic barrier or shield, said magnetic isolating piece is made of pure iron or alloy with a thickness of at least 0.20 mm, the ratio of the thickness and minimum periphery of the magnetic isolating piece to those of the magnetic body being in the range of 1:(1-4) and (1-4):1 respectively.

5. The wrist watch with health care function according to claim 3 wherein said magnetic isolating body is a magnetic isolating piece covered on the magnetic body and attached in the back cover to form a magnetic barrier, said magnetic isolating body is made of pure iron or alloy, its thickness is at least 0.20 mm, the ratio of the thickness and minimum periphery of the magnetic isolating piece to those (thickness and periphery) of the magnetic body being in the range of 1:(1-4) and (1-4):1 respectively.

6. The wrist watch with health care function according to claim 4 or 5 wherein both said magnetic isolating body said magnetic body are circular, with the ratio of their diameters is the range of (1-4):1.

7. The wrist watch with health care function according to claim 1 or 3 wherein said magnetic isolating body is the back cover itself of the wrist watch.

8. The wrist watch with health care function according to claim 1 or 3 wherein said magnetic isolating body is a ⊔-shaped magnetic isolating shield placed in the back cover.

9. The wrist watch with health care function according to claim 7 wherein the magnetic body and the corresponding cavity receiving said magnetic body are placed in the outer side of the back cover close to the wrist.

10. The wrist watch with health care function according to claim 8 wherein said ⊔-shaped magnetic isolating shield and the corresponding cavity receiving the magnetic body are placed in the inner side of the back cover opposite to the mechanism (core) of the wrist watch.

11. The wrist watch with health care function according to claim 8 wherein said ⊔-shaped magnetic isolating shield and the corresponding cavity receiving said magnetic body are placed in the outer side of the back cover.

12. The wrist watch with health care function according to claim 2 wherein said magnetic body is made of permanent magnetic materials with the magnetic induction ranging from 100-400 mili-Tesla, the volume of the magnetic body being matched with that of the corresponding cavity.

* * * * *